United States Patent
Bogdanowicz et al.

(10) Patent No.: US 9,114,059 B2
(45) Date of Patent: Aug. 25, 2015

(54) METHOD AND APPARATUS FOR MONITORING MANUAL CHEST COMPRESSION EFFICIENCY DURING CPR

(75) Inventors: Leszek Bogdanowicz, Park Ridge, IL (US); Brian J. Skelton, Lake Zurich, IL (US); Michael C. Garrett, Wilmette, IL (US)

(73) Assignee: ZOLL Medical Corporation, Chelmsford, MA (US)

( * ) Notice: Subject to any disclaimer, the term of this patent is extended or adjusted under 35 U.S.C. 154(b) by 216 days.

(21) Appl. No.: 13/559,955

(22) Filed: Jul. 27, 2012

(65) Prior Publication Data
US 2013/0030326 A1    Jan. 31, 2013

Related U.S. Application Data

(60) Provisional application No. 61/512,360, filed on Jul. 27, 2011.

(51) Int. Cl.
*A61H 31/00* (2006.01)
*A61H 31/02* (2006.01)
*A61N 1/39* (2006.01)

(52) U.S. Cl.
CPC ...... *A61H 31/007* (2013.01); *A61H 2201/1619* (2013.01); *A61H 2201/5007* (2013.01); *A61H 2201/5043* (2013.01); *A61H 2201/5048* (2013.01); *A61H 2201/5061* (2013.01); *A61H 2201/5097* (2013.01); *A61N 1/3993* (2013.01)

(58) Field of Classification Search
CPC .................................................. A61H 31/007
USPC ................... 600/587, 595; 601/41; 606/192; 128/207.14
See application file for complete search history.

(56) References Cited

U.S. PATENT DOCUMENTS

| | | | | |
|---|---|---|---|---|
| 5,830,160 | A * | 11/1998 | Reinkensmeyer | 600/595 |
| 7,605,804 | B2 * | 10/2009 | Wilson | 345/173 |
| 2002/0167486 | A1 * | 11/2002 | Tan et al. | 345/156 |
| 2002/0193711 | A1 | 12/2002 | Halperin et al. | |
| 2006/0019229 | A1 | 1/2006 | Morallee et al. | |
| 2008/0300517 | A1 * | 12/2008 | Nysaether | 601/41 |
| 2010/0228166 | A1 * | 9/2010 | Centen | 601/41 |
| 2010/0256539 | A1 | 10/2010 | Strand et al. | |

FOREIGN PATENT DOCUMENTS

WO    WO2010148078    12/2010

* cited by examiner

*Primary Examiner* — Brian Szmal
(74) *Attorney, Agent, or Firm* — K. David Crockett, Esq.; Paul J. Backofen, Esq.; Crockett & Crockett, PC

(57) ABSTRACT

The compression measurement and feedback system measures the magnitude and the angle of manual CPR force applied to a patient and provides the measured magnitude and direction information as compression data feedback to the person applying CPR to the patient. Any variation in the magnitude or direction of the compression force applied may be calculated from the compression data measured by the compression sensor. A monitor receives the compression data and processes the compression data to generate feedback data to the CPR provider indicating the magnitude and direction of the applied CPR compression along with ideal CPR compression characteristics for comparison.

4 Claims, 4 Drawing Sheets

METHOD AND APPARATUS FOR MONITORING MANUAL CHEST COMPRESSION EFFICIENCY DURING CPR

RELATED APPLICATIONS

This application claims priority from U.S. Provisional application 61/512,360 filed Jul. 27, 2011.

FIELD OF THE INVENTIONS

The inventions described below relate the field of Cardio Pulmonary Resuscitation (CPR) and more specifically to feedback systems for CPR providers to optimize CPR effectiveness.

BACKGROUND OF THE INVENTIONS

Sudden cardiac arrest is a leading cause of death with approximately 250,000 deaths per year in the U.S. occurring outside a hospital setting. CPR is an emergency first aid procedure for a victim of sudden cardiac arrest. Performance of CPR creates blood circulation in the victim by periodically compressing the victim's chest.

Administration of CPR is a physically demanding procedure and the effectiveness of CPR administered by an amateur is variable and the studies suggest only around half of bystander CPR is performed correctly. Additional studies have shown that half of chest compressions administered by health care professionals are also too shallow.

Chest compression monitoring during the course of CPR is now possible with the Real CPR Help® technology marketed by ZOLL Medical Corporation. This technology is described in U.S. Pat. Nos. 6,390,996, 7,108,665, and 7,429,250, and includes the use of an accelerometer to measure accelerations of the chest and calculating the depth of each compression from the acceleration signal. The technology is used in ZOLL's Real CPR Help® compression depth monitoring system to provides real-time rate and depth CPR feedback for manual CPR providers. Commercially, it is implemented in ZOLL's electrode pads, such as the CPR-D•padz® electrode pads. It is also implemented for training use in the iPhone app PocketCPR®. The same technology can be provided in automatic CPR chest compression devices, such as ZOLL Circulation's AutoPulse® chest compression device, which is described in numerous patents issued to ZOLL Circulation such as U.S. Pat. No. 6,066,106 and its continuations.

The Real CPR Help® compression depth monitoring system provides valuable unambiguous feedback during manual CPR, because the accelerometer is fixed to the chest of the patient either because is it fixed to electrode pads that are fixed to the patients chest with adhesive, or because it is fixed relative the CPR providers hands which the CPR provider maintains in the appropriate location over the sternum of the patient. Chest compression information that might be provided during automated CPR with the AutoPulse® device may be unambiguous, assuming that the compression belt used with the AutoPulse® device does not shift during the course of treatment. While this may be monitored visually by an EMT using the AutoPulse®, the system can be improved by providing some mechanism for determining compression depth in the case where the compression belt shifts up or down on the patient's chest during use.

SUMMARY

The devices and methods described below provide for a compression sensor to measure the efficiency of CPR compressions and provide feedback to the CPR provider to facilitate the effective administration of cardio pulmonary resuscitation. The compression sensor and feedback system produces an output indicative of the magnitude, angle and frequency of applied chest compressions. Proper CPR is administered when chest compressions have a near zero angle of displacement from a vertical line drawn through a victims sternum, heart and spine as well as a magnitude that produces a compression depth of 1.5-2 inches (3-6 cm) depth and a frequency that meets American Heart Association (AHA) guidlines. Coupled with an automated external defibrillator (AED), monitor, monitor/defibrillator or other suitable apparatus, the compression sensor feedback system provides audible and or visual feedback to an administrator of CPR to correct chest compression angle of each applied compression. The visual feedback may be textual or graphical.

The compression measurement and feedback system includes a compression sensor with an array of measurement elements, each measurement element generating compression data from the start of a compression through the end of the compression. Calculations performed on the compression data yields an angle and the magnitude of the applied compression. Audible and or visual feedback is provided to the administrator of compressions to correct the angle of compressions as necessary. The resulting feedback and measuring system provide an efficient chest compression system.

The compression measurement and feedback system measures the magnitude and the angle of manual CPR force applied to a patient. A compression sensor measures the magnitude and direction of CPR compression force applied to the patient undergoing CPR and provides the measured magnitude and direction information as compression data to a monitor. Any variation in the magnitude or direction of the force applied may be calculated from the compression data measured by the compression sensor. The monitor receives the compression data and processes the compression data to generate feedback data to the CPR provider indicating the magnitude and direction of the applied CPR compression along with ideal CPR compression characteristics for comparison.

A compression measurement and feedback system includes a compression sensor for measuring the magnitude and direction of CPR compression force applied to a patient undergoing CPR. The compression sensor provides the measured magnitude and direction information as compression data to a monitor. The compression sensor includes a generally planar disk having a central axis perpendicular to the disk. The disk may be secured to a printed circuit board oriented parallel to the disk. The printed circuit board includes one or more compression sensors on the sensor surface to generate compression data. The compression sensor also includes a polymer disk or dome secured to the sensor surface of the printed circuit board. The printed circuit board also includes a means for collecting compression data and transferring the compression data to the monitor. The monitor receives the compression data and processes the compression data to generate feedback data to the CPR provider indicating the magnitude and direction of the applied CPR compression along with ideal CPR compression characteristics for comparison.

The amount of compression force measured by the compression sensor is a function of the compressibility of the polymer disk or dome that suspends a magnet above an array of magnetic sensors. The displacement of the magnetic field components measured by the magnetic sensors is therefore a function of the directional force vector applied to the device. The feedback from the monitor enables a CPR provider to minimize or eliminate horizontal force components and provide more efficient and effective CPR.

Alternatively, the magnet and magnetic sensors may be replaced by orthogonal strain measuring members, which deflect under multi directional force, allowing the measurement of the applied force vector.

A conductive layer may be formed in or on the polymer disk or dome and a capacitive plate array may be formed on the printed circuit board. During CPR compressions, the plate array is scanned and the parasitic capacitance changes as the conductive layer of the compression sensor comes nearer the capacitive plate. As the conductive layer nears the capacitive array the parasitic capacitance changes in that area and thus the vertical and angular displacement can be measured.

The polymer disk or dome may be used to suspend a reflective mirror above a light source and light sensors. The measured magnitude of CPR compression force applied by a provider is a function of the material that suspends the conical mirror or other suitable reflector above the light source. The conical nature of the reflector when oriented over the center of the light source will evenly distribute light to photodiode arrays oriented about the center of the sensor. As the compression increases and or the angular displacement changes, the photodiode array illumination will change. The displacement of the reflective element is therefore a function of the directional force vector applied to the device.

The compression measurement and feedback system may also include a two-wire communications system and protocol which allows a minimum number of connections between the wired compression sensor and the AED, monitor, or monitor/defibrillator. This reduced number of connections increases the measurement capability of the compression sensor, while also increasing reliability of the interconnections. The two-wire connection system both powers the compression sensor and allows digital or analog communications between the compression sensor and the AED.

The devices and methods described below provide for a compression sensor to measure the magnitude and the angle of the applied CPR compressions as compression data. The measured CPR compression data is used to provide feedback to the CPR provider to reduce or eliminate horizontal CPR forces and facilitate the effective administration of cardio pulmonary resuscitation.

DETAILED DESCRIPTION OF THE INVENTIONS

Figure 1:
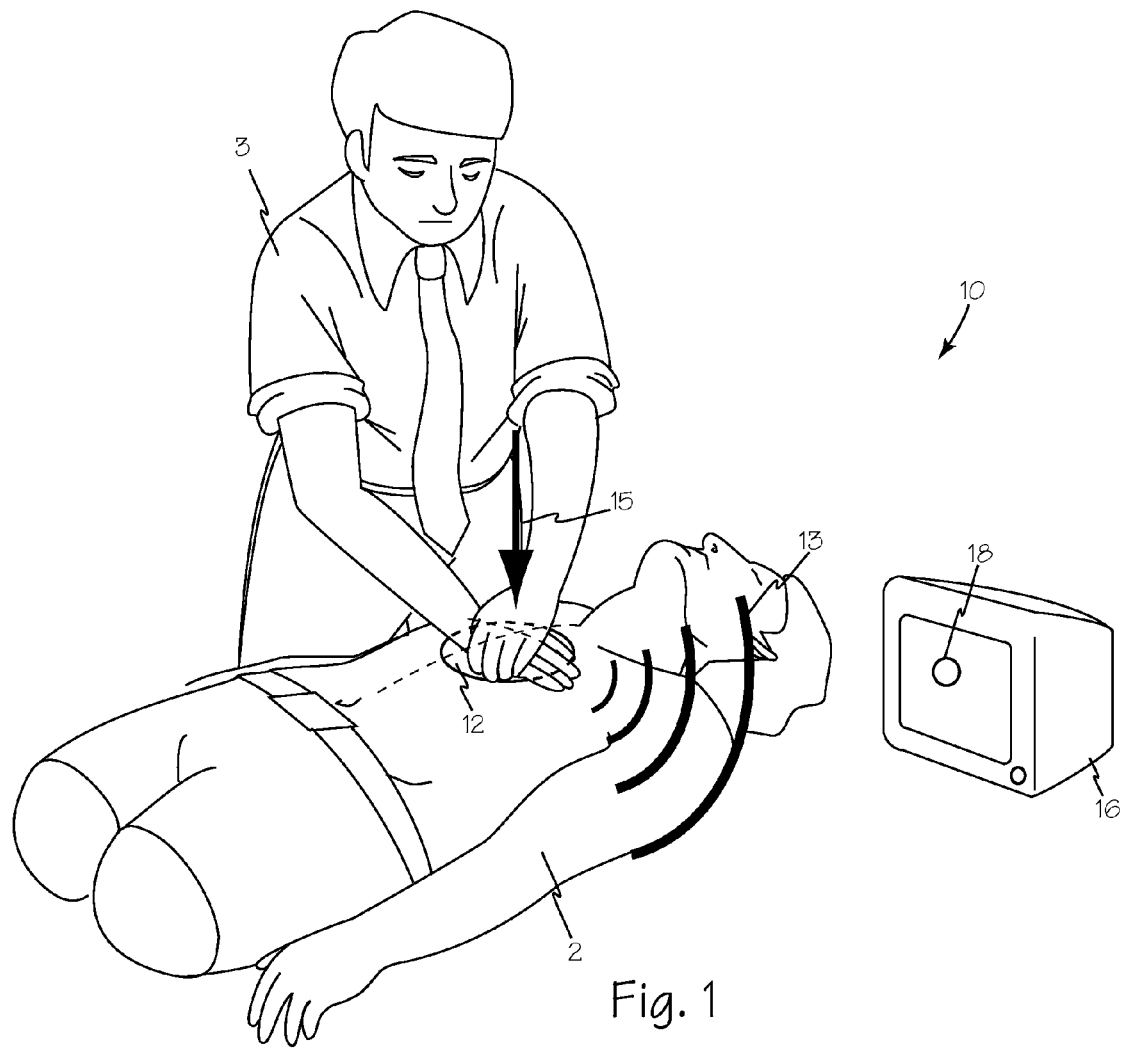
FIG. 1 is a perspective view of a CPR provider performing CPR on a victim with a compression sensor and feedback display.

FIG. 1 illustrates cardiac arrest victim 2 receiving CPR from CPR provider 3 using compression measurement and feedback system 10. CPR provider 3 performs manual CPR by applying compression force to compression sensor 12. Signals such as signals 13 representing the magnitude and direction of compression force 15 are transmitted to a coupled AED, monitor, monitor/defibrillator or other suitable apparatus such as AED monitor 16. Signals 13, representing the applied compression force and any other suitable signals may be transmitted to AED 16 using wires, wireless system and use any suitable communications protocol. Monitor 16 receives signals 13 from compression sensor 12 and processes the signals and generates one or more audible and or visual cues such as feedback display 18 to prompt provider 3 to optimize compression force 15 and angle of application to improve the application of manual CPR and to provide more consistent application of manual CPR.

Figure 3:
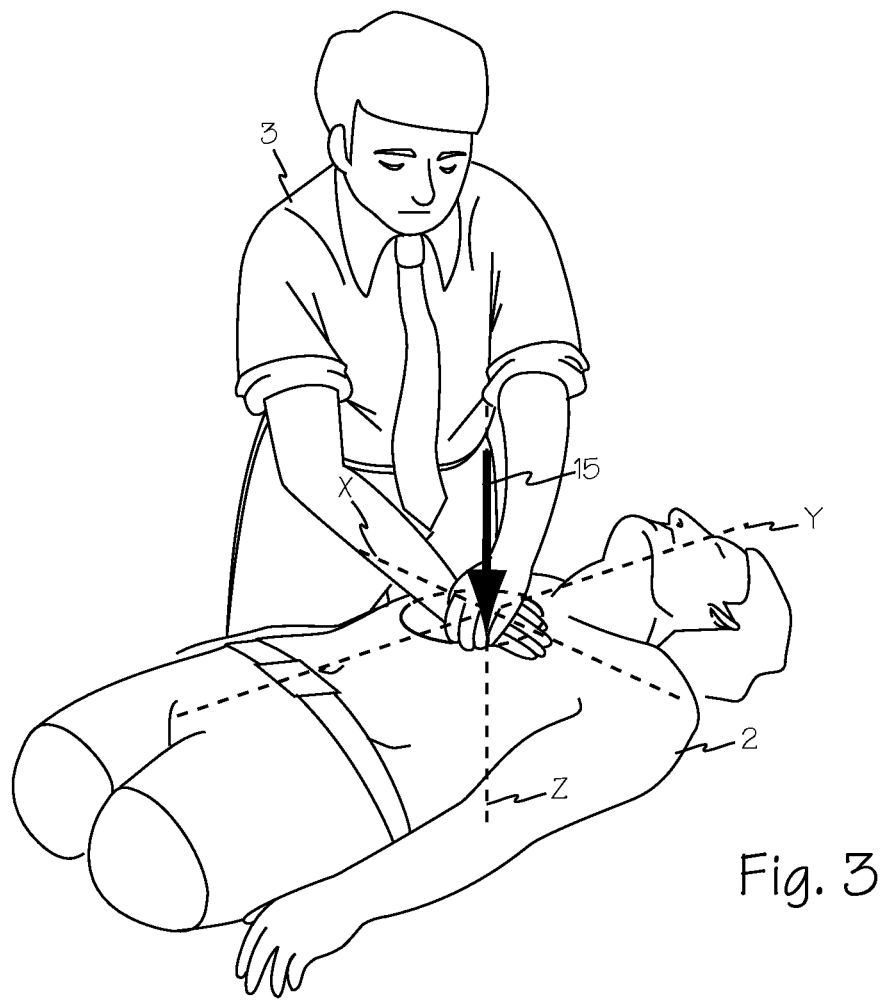
FIG. 3 is a perspective view of a CPR provider performing CPR on a victim illustrating the reference axes.

Referring now to FIG. 3, during the practice of manual CPR, a CPR provider such as CPR provider 3 repeatedly applies compression force 15 to the victims chest. Ideally, a CPR compression force is a vector 15 applied along the Z-axis which corresponds to a line drawn between the victims spine and the sternum which includes the heart. When a CPR provider is inexperienced, stressed or tired they tend to apply compression force at an angle with a significant wasted horizontal force. By applying compression force at an angle off the vertical axis, the magnitude of the useful force along the vertical or Z-axis is less than ideal.

Figure 4:
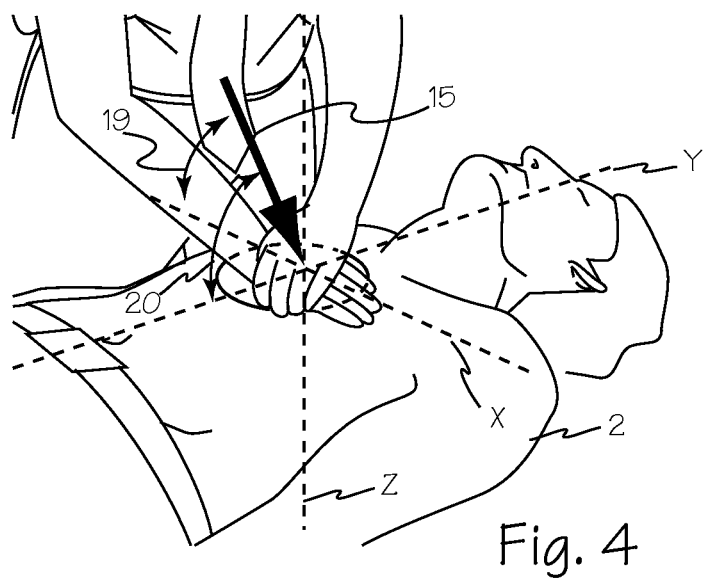
FIG. 4 is a perspective view of the reference axes illustrating compression measurement elements.

Referring now to FIG. 4, first angle 19 represents the angular deviation of compression force 15 along the X-axis, the lateral axis of the patient, and second angle 20 represents the angular deviation of compression force 15 along the Y-axis, the superior-inferior axis of the patient.

Figure 5:
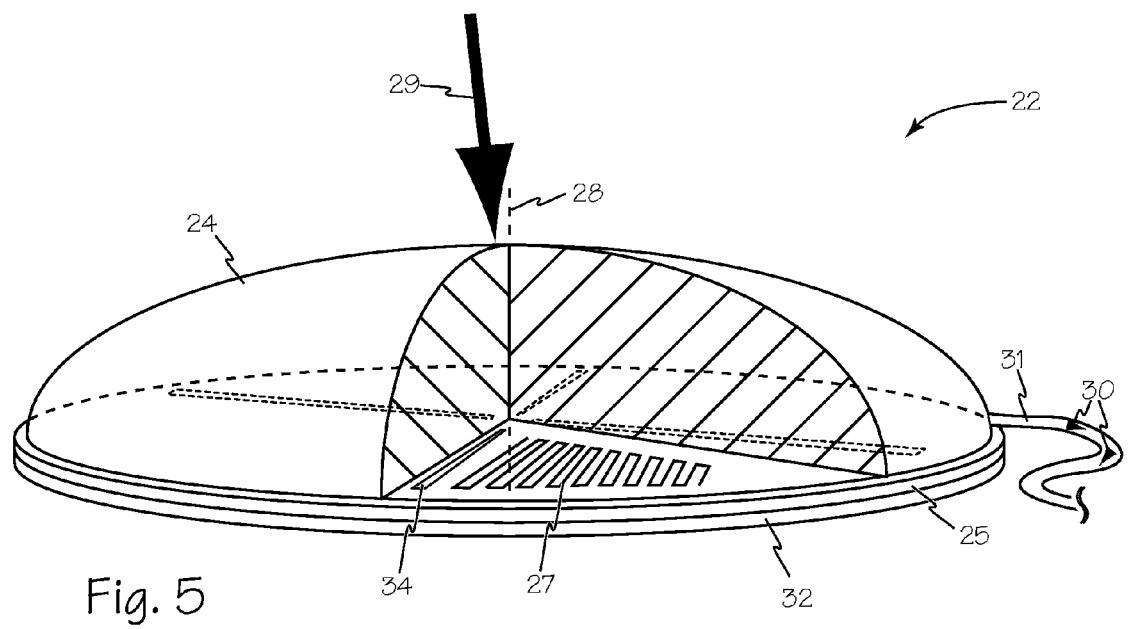
FIG. 5 is a perspective view of a compression sensor with strain gauges.

Compression sensor 22 of FIG. 5 includes polymer compression pad 24 formed on or secured to printed circuit board 25 (PCB). Polymer compression pads such as compression pad 24 may adopt a disk shape, a dome shape or any other suitable shape. Circuit board 25 is a generally planar disk perpendicular to the Z-axis or central axis 28 and it includes one or more strain gauge sensors such as sensor 27 formed in or on the printed circuit board. The sensors are arranged around central axis such that when a compression force such as force 29 is applied to compression sensor 22, variations in the force registered by different sensors around central axis 28 may be used to determine the magnitude and direction of force 29. Any angular deviation of force 29 from the Z-axis or central axis 28 is provided to a CPR provider in the form of audible of visual feedback to prompt the CPR provider to properly orient the compression force and optimize the magnitude of the compression force.

Compression data 30 is conducted from compression sensor 22 using multi-conductor cable 31 to any suitable AED, monitor, monitor/defibrillator or other suitable apparatus such as AED 16 of FIG. 1. Compression data 30 may be transferred via cable such as cable 31 or wirelessly.

Printed circuit board 25 may also include one or more slots, cuts or other points of flexibility such as slots 34 to enable limited flexure of the printed circuit board during CPR. Printed circuit board 25 and mechanical layer 32 may also be shaped to conform to the shape of a human sternum to minimize mechanical flexure during the application of CPR compressions. One or more additional layers such as mechanical layer 32 may be bonded to printed circuit board 25 to provide additional mechanical strength to the printed circuit board. The one or more mechanical layers and the printed circuit board are all generally planar and are generally oriented in the plane formed by the X-axis and the Y-axis and are thus perpendicular to the Z or central axis. Polymer disk 24 is formed of any suitable polymer or polymer foam with a known compressibility.

Figure 6:
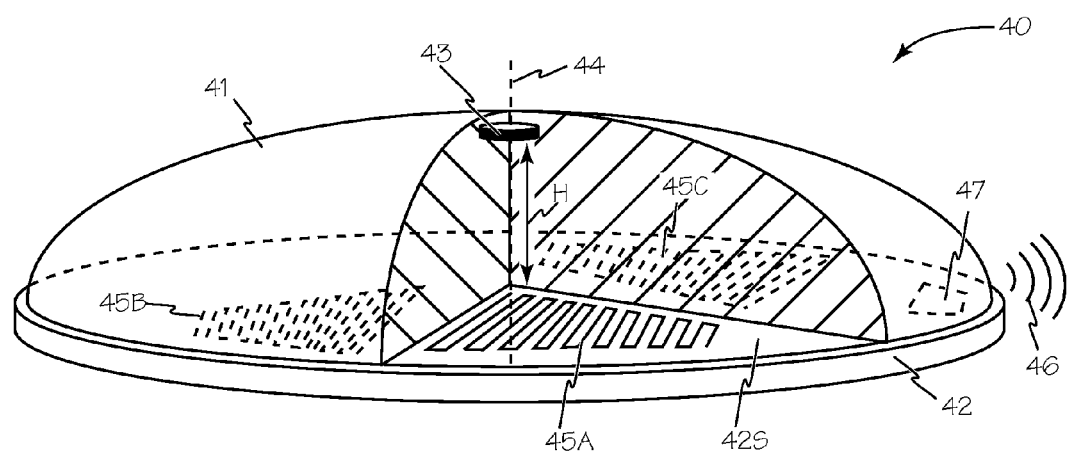
FIG. 6 is a perspective view of a compression sensor with a magnet and magnetic field sensors.

Referring now to FIG. 6, compression sensor 40 includes polymer dome 41 secured to printed circuit board 42. Polymer disk 41 includes permanent magnet 43 embedded in the polymer at a distance H from sensor surface 42S and centered on Z-axis or central axis 44. Printed circuit board 42 includes an array of magnetic sensors such as sensors 45A, 45B and 45C oriented around central axis 44. As a compression force is applied to polymer dome 41, the polymer dome is compressed and magnet 43 is forced closer to printed circuit board 42 and magnetic sensors 45A, 45B and 45C. Any application of compression force oriented off axis from central or Z-axis 44 will result in variations in compression sensor data 46 from the magnetic sensors. Compression sensor data 46 is conducted to transmitter 47 where the compression sensor data is transmitted to any suitable AED, monitor, monitor/defibrillator or other suitable apparatus such as AED 16 of FIG. 1 for processing and presentation as feedback display 18.

In use, a compression sensor such as compression sensor 40 is placed on a patient's sternum at the point where manual CPR force is to be applied. The provider of manual CPR places their hands on the compression sensor and applies force to the compression sensor as shown in FIG. 1. The force applied to the compression sensor is transferred through the compression sensor to the patient's sternum, compressing the heart. The compression sensor gathers compression data corresponding to the magnitude and direction of the force applied. The compression data is transferred to a suitable monitor for processing and display of the feedback signals to the CPR provider. Any variation in the magnitude or direction of the force applied may be calculated from the compression data measured by the compression sensor and the variations are presented to the CPR provider as feedback to optimize the compression magnitude and direction.

Figure 2:
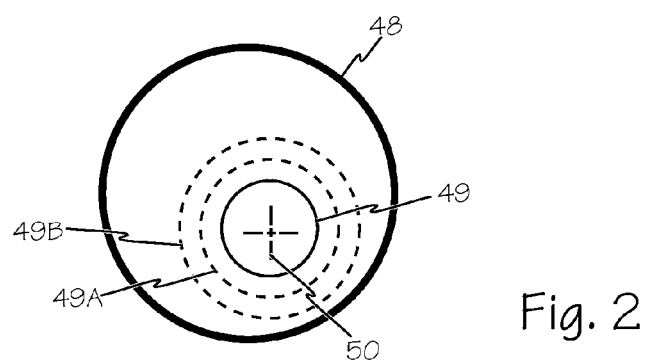
FIG. 2 is a representation of a graphical user interface for providing CPR feedback.

Referring now to FIG. 2, a graphical user interface to provide feedback to a CPR provider may include a circle or other suitable shape to represent an ideal complete compression such as circle 48. Within the ideal compression circle is a small filled bubble or other shape such as bubble 49 representing the applied compression force. As a CPR compression is applied, the bubble 49 expands as illustrated by bubbles 49A and 49B according to the compression data processed by the monitor. To provide feedback on the direction of the applied compression, bubble 49 may move within the ideal compression circle. Alternatively, a small crosshair or other suitable marker such as crosshair 50 represents the center of the applied compression force and crosshair 50 is moved relative to the ideal compression circle according to the compression data.

In use, the PCB disk such as disk 42 is generally placed in contact with the patient's chest and the CPR provider applies force to the polymer compression pad for application of CPR. However, the compression sensor may be oriented with the polymer compression pad in contact with the patient's chest and the CPR provider's hands provide force directly to the PCB disk.

Figure 7:
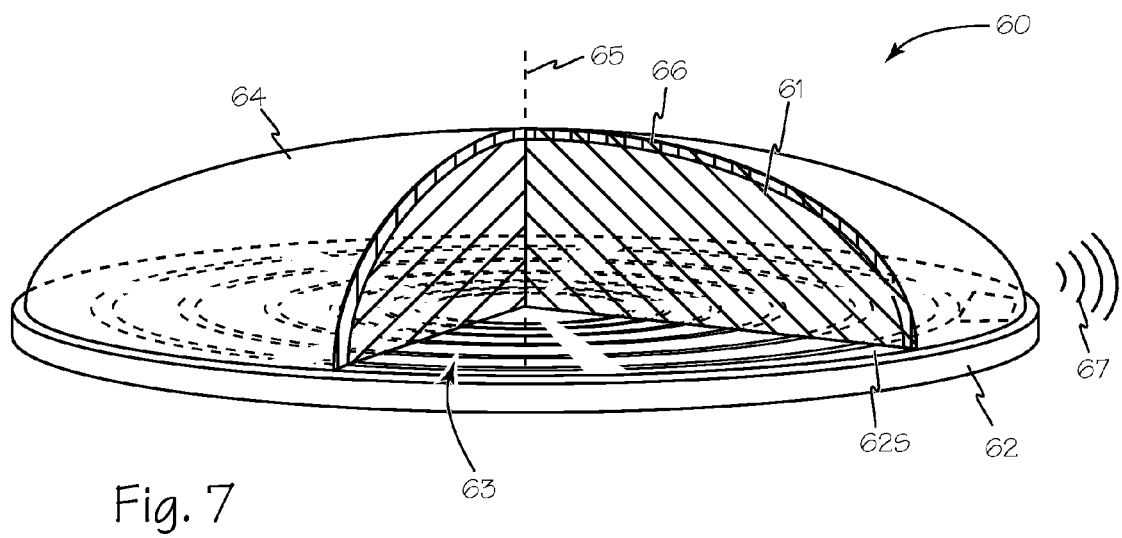
FIG. 7 is a perspective view of a compression sensor with capacitive sensors.

Referring now to FIG. 7, compression sensor 60 includes polymer disk 61 bonded to sensor surface 62S of printed circuit board 62. Sensor surface 62S includes capacitive plate arrays 63 for measuring magnitude and direction of a CPR compression applied to upper surface 64 generally along central or Z-axis 65. Conductive layer 66 is secured over polymer disk 61 with polymer disk 61 between capacitive plate arrays 63 and conductive layer 66. Capacitive plate arrays 63 are generally annual arc shaped and are arranged around central axis 65. In use, capacitive plate arrays 63 are scanned and the parasitic capacitance changes as conductive layer 66 is compressed closer to printed circuit board 62. Depending on the magnitude and direction of the applied compression force, the parasitic capacitance will change in different capacitive plate arrays producing compression data 67 corresponding to the magnitude and direction of the applied compression force.

Figure 8:
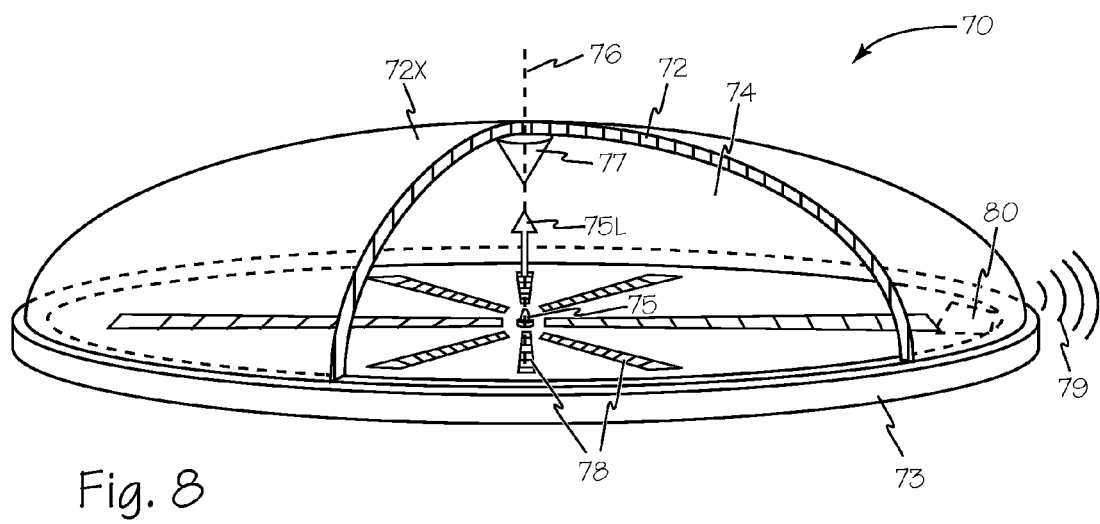
FIG. 8 is a perspective view of a compression sensor with a reflector and light sensor arrays.

Referring now to FIG. 8, illuminated compression sensor 70 includes polymer shell 72, bonded to, secured to or otherwise engaging printed circuit board 73 and enclosing interior volume 74. Interior volume 74 may be filled with any material having light transmission characteristics suitable to enable light 75L emitted from light source 75 along central axis 76 to reflect from reflector 77 and be received by light sensor arrays such as light sensor arrays 78. Compression force applied to outer surface 72X that has any lateral component will cause reflector 77 to reflect light 75L disproportionately to light sensor arrays 78 which will yield direction data and the relative intensity of light reflected to all the light sensor arrays will be proportional to the magnitude of compression force applied to the compression sensor. Collectively the magnitude and direction information will be transmitted as compression data. Each light sensor array generates compression data 79 which may be collected by data unit 80 which formats the compression data for wireless or wired transmission to a monitor for processing and display. Light source 75 may be any suitable source of electromagnetic energy such as an LED or solid state laser.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A CPR compression sensor feedback system comprising:
   a compression sensor means for measuring the magnitude and direction, relative to orthogonal X, Y and Z axes, of CPR compression force applied to a patient undergoing CPR and providing the measured magnitude and direction information as compression data;
   a monitor means for receiving the compression data and processing the compression data to generate feedback data to the CPR provider indicating the magnitude and direction of the applied CPR compression along with ideal CPR compression characteristics for comparison; and
   wherein the feedback data related to the direction of the CPR compression force provides deviation from the Z-axis along both the X-axis and the Y-axis.

2. A CPR compression sensor feedback system comprising:
   a compression sensor means for measuring the magnitude and direction of CPR compression force applied to a patient undergoing CPR and providing the measured magnitude and direction information as compression data;
   a monitor means for receiving the compression data and processing the compression data to generate feedback data to the CPR provider indicating the magnitude and direction of the applied CPR compression along with ideal CPR compression characteristics for comparison;

a graphical user interface consisting of a circle representing an ideal complete compression and a small filled bubble in the center of the circle representing the applied force in which the monitor is operable to expand the filled bubble according to the compression data as compression force is applied; and a small crosshair representing the center of the applied compression force and the monitor is operable to move the crosshair relative to the ideal compression circle according to the compression data.

3. A CPR compression sensor feedback system comprising:

a compression sensor operable to measure the magnitude and direction, relative to orthogonal X, Y and Z axes, of CPR compression force applied by a CPR provider to a patient undergoing CPR and provide the measured magnitude and direction information as compression data;

a monitor operable to receive the compression data and process the compression data to generate feedback data to the CPR provider indicating the magnitude and direction of the applied CPR compression along with ideal CPR compression characteristics for comparison; and wherein the feedback data related to the direction of the CPR compression force identifies deviation of the force applied by the CPR provider from the Z-axis along both the X-axis and the Y-axis.

4. A CPR compression sensor feedback system comprising:

a compression sensor operable to measure the magnitude and direction of CPR compression force applied by a CPR provider to a patient undergoing CPR and provide the measured magnitude and direction information as compression data;

a monitor operably connected to the compression sensor, the monitor operable to receive the compression data and process the compression data to generate feedback data to the CPR provider indicating the magnitude and direction of the applied CPR compression along with ideal CPR compression characteristics for comparison;

a graphical user interface consisting of a circle representing an ideal complete compression and a small filled bubble in the center of the circle representing the applied force in which the monitor is operable to expand the filled bubble according to the compression data as compression force is applied; and a small crosshair representing the center of the applied compression force and the monitor is operable to move the crosshair relative to the ideal compression circle according to the compression data.

\* \* \* \* \*